United States Patent [19]

Mason et al.

[11] Patent Number: 4,938,777
[45] Date of Patent: Jul. 3, 1990

[54] ANKLE ORTHOSIS

[75] Inventors: Jeffrey T. Mason, Escondido; Patrick W. Cawley, San Diego; Bradley R. Mason, Carlsbad, all of Calif.

[73] Assignee: Donjoy Corporation, Carlsbad, Calif.

[21] Appl. No.: 60,608

[22] Filed: Jun. 11, 1987

[51] Int. Cl.$^5$ ............................................... A61F 2/66
[52] U.S. Cl. ..................................... 623/50; 623/52; 623/27; 128/80 H
[58] Field of Search ............... 128/80 H, 80 J, 77, 128/80 R, 80 A, 80 P, 80 C, 80 D, 80 DB, 80 E, 80 F, 80 G

[56] References Cited

U.S. PATENT DOCUMENTS

| 2,525,237 | 10/1950 | Park | 128/80 E |
| 4,289,122 | 9/1981 | Mason | 128/80 H |
| 4,351,324 | 9/1982 | Broukhoust | 128/80 J |
| 4,554,912 | 11/1985 | Haberman | 128/80 J |
| 4,665,904 | 5/1987 | Lerman | 128/80 H |

Primary Examiner—Richard J. Apley
Assistant Examiner—David Willse
Attorney, Agent, or Firm—Stanley A. Becker; Dinah Newton-Hill

[57] ABSTRACT

An ankle orthosis device is described which comprises a foot receiving cup or shoe which is integrated with or to which is rigidly attached a force transmitting rib which has an inverted Y-shape. At the proximal end of the Y is slidably attached to the rib for securing the device to the lower leg near the distal end of the tibia. Inversion or eversion torque producing forces applied to the device are transmitted through the cup or shoe and rib to the tibia so that there is no tendency to produce injury causing inversion or eversion of the ankle as a result of the torque. Generally free movement in dorsiflexion and plantar flexion is permitted by the device, which allows it to be used for walking, running, sports events and the like, as well as being useful in a postoperative or other therapeutic ankle treatment program. The device can be in the form of shoe inserts, attached to the heel of a shoe or incorporated into the body of a shoe. The devices can easily be manufactured in a few, widely usable sizes, since no custom fitting is required.

24 Claims, 2 Drawing Sheets

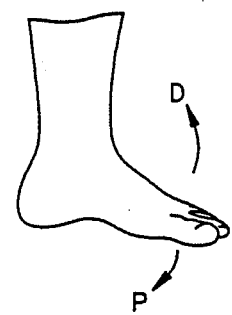
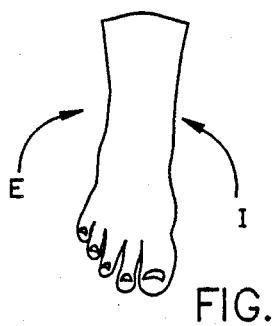
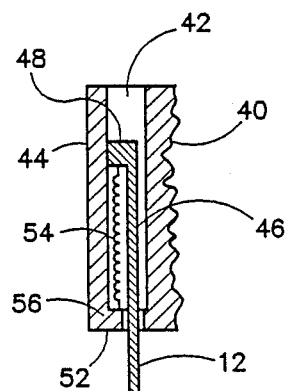
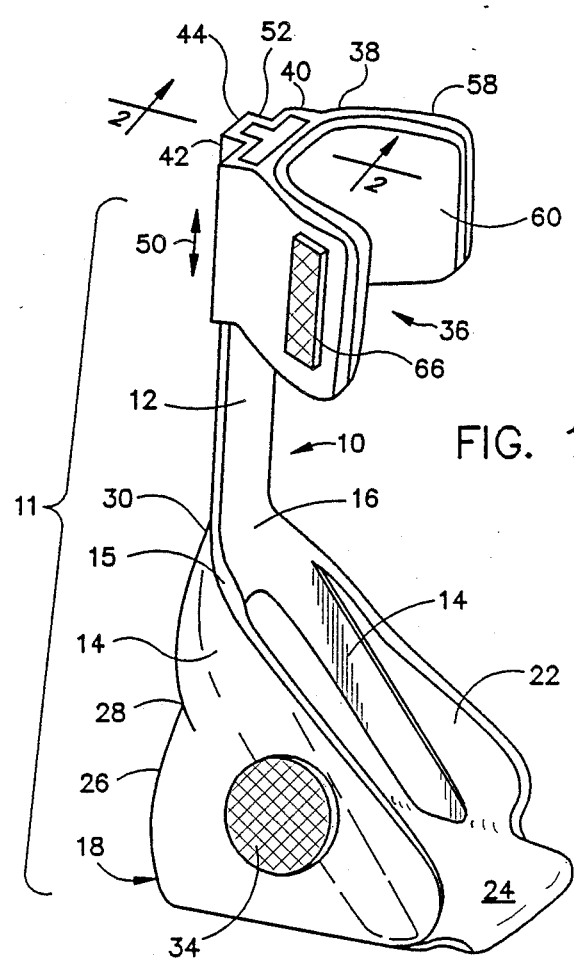
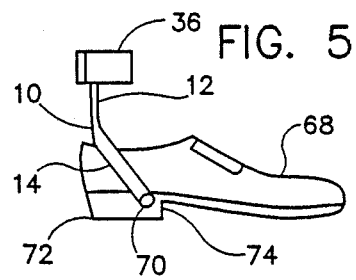
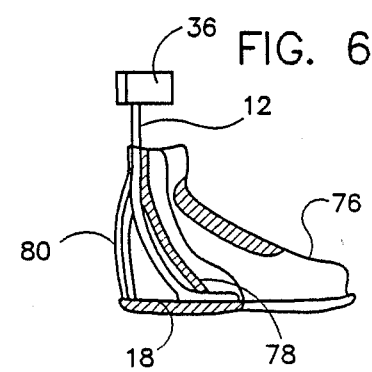

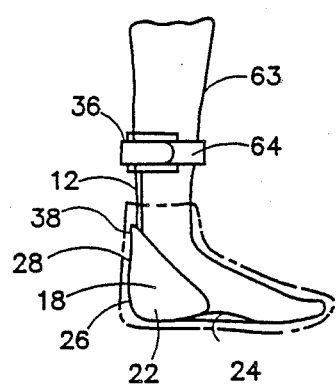
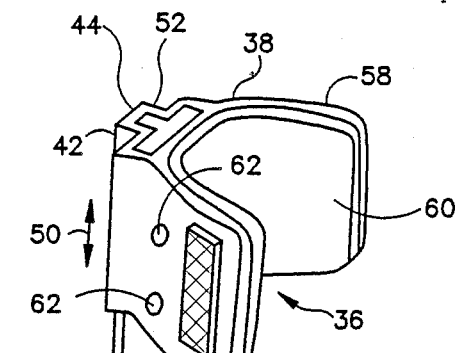
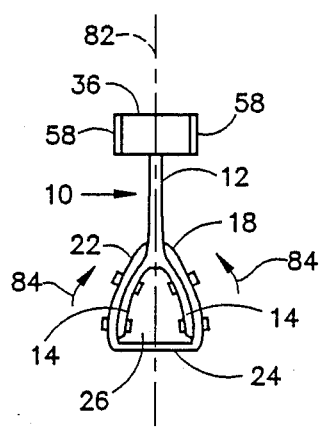
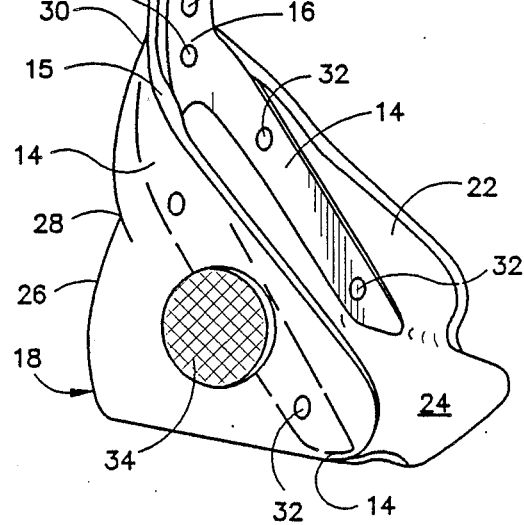
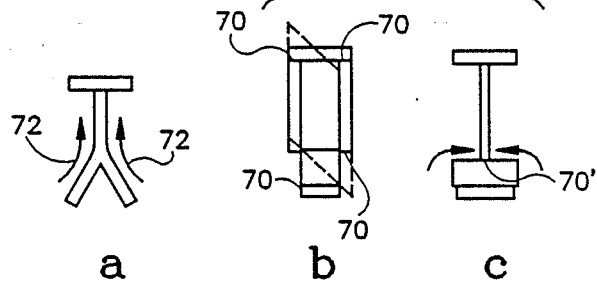

ANKLE ORTHOSIS

FIELD OF THE INVENTION

The invention herein relates to ankle orthoses. More particularly it relates to ankle orthoses which are useful in both athletic and medical applications.

BACKGROUND OF THE INVENTION

The normal movements of the human ankle during activities such as walking, running and various types of athletics are, as illustrated in FIG. 8, dorsiflexion D and plantar flexion P, both of which occur in a sagittal plane. For such activities it is important that these types of flexion not be unduly restricted.

Conversely, the ankle is not normally intended to move abruptly or excessively in inversion I or eversion E as illustrated in FIG. 7. While a person does make slight inversion and eversion movements of the ankle in walking and athletics, external forces to which the ankle is subject can cause undue, excessive or abrupt inversion or eversion torque which results in serious ankle injury. For instance, during sports an athlete can step or land heavily on the side of his or her foot, or a walker can accidentally step off the side of a curb or have his or her ankle turned by stepping on an irregular patch of ground or sidewalk.

In addition to such type of ankle injuries, ankle motion frequently needs to be controlled after surgical procedures. It is common for those recovering from foot, ankle or leg surgery to go through several phases of protective devices following the surgery until the foot, ankle or leg is completely healed and rehabilitated. The early phases often involve complete immobilization of the ankle while later phases involve less restrictions on movement. Throughout all the phases, however, good recovery normally requires that excessive inversion and eversion be completely avoided. It is also not uncommon for a physician to recommend that even after healing and rehabilitation the patient take precautions against incurring abrupt or excessive inversion or eversion.

Over the years there have been many approaches to preventing injurious inversion and eversion ankle motions. Most have involved means of immobilizing the ankle to various degrees. One common technique widely used in sports is to provide a tight tape binding around the ankle and longitudinal arch of the foot. This is of somewhat limited effectiveness, however, for the tape cannot be so tight as to restrict the athlete from running, jumping or performing similar motions required by the sport, and therefore the tape is of little effectiveness against the more severe forces that cause injury. Further, tape cannot be left in position for more than a few hours, is relatively uncomfortable to the athlete and is difficult to apply properly (often requiring the assistance of another person such as a sports trainer).

Numerous mechanical devices, commonly known as ankle-foot orthoses ("AFO's") have been developed to deal with plantar flexion and dorsiflexion problems. Such problems may arise from illnesses, such as polio, and prevent a person from being able to control flexion of the ankle (commonly called "drop foot"), or may result from ankle injuries. These AFO's can be grouped into two categories: those which are analogous to tape wrapping systems, usually having a preformed type of wrapping, and those which use mechanical leg braces. The latter are more pertinent to the present invention. Many patents illustrate examples of these types.

A good description of representative examples of the leg brace type is found in the *Atlas of Orthotics* (2d edn.; 1985), published by the American Academy of Orthopaedic Surgeons, in chapter 10, "Lower-Limb Orthoses" by S. Fishman et al. These can be considered to have a "parallelogram" structure if viewed from the anterior or posterior direction, as illustrated in FIG. 10B. AFO's are designed solely to limit, assist or restrict plantar flexion and/or dorsiflexion. They do not effectively deal with inversion and eversion, nor are they designed to do so.

In addition, AFO's suffer from a variety of disadvantages:

1. The leg braces are rigid and any flexural motion of the foot comes only through the use of complicated hinge mechanisms. These hinge mechanisms in turn must usually have complex built-in stops to prevent excessive flexion. Other accommodation to the rigidity is obtained through added structures of resilient padding or springs to allow motion.

2. The rigidity of the braces can cause abrasion of the calf muscles as the user walks.

3. The rigidity limits the use of the AFO's so that they cannot be effectively worn for sports or other activities in which running, jumping and similar leg, ankle and foot movements are necessary.

4. The leg brace AFO's generally require the use of a sturdy shoe to be effective. Even those which involve shoe inserts still require a wide shoe with little flexibility to accommodate the metal braces and hinge mechanisms. This effectively precludes the use of AFO's in soft shoes such as athletic shoes.

5. Virtually all AFO's must be custom fitted to the individual user, to accommodate the user's feet and legs.

6. The AFO's are unsightly, and because of their spread configuration they are difficult to conceal under trousers.

7. Because of their spread configuration and lateral orientation to the leg, they are also hazardous to other individuals with whom the user may come into physical contact. For example, if an athlete were to use a leg brace AFO during a contact sporting event such as basketball (notwithstanding the rigidity problems), other players would be at risk of receiving lacerations, bruises or other injuries to their lower legs by hitting the braces during play.

Other types of AFO's act through a single brace aligned posterior to the lower leg and in the same sagittal plane. Typically these AFO's attach to the heel of a shoe. They have no ability to resist inversion or eversion torque since they are aligned along the center line of the ankle and foot and therefore have no resistive moment arm. The shoe cannot serve to transfer lateral forces to the central brace since it is not sufficiently rigid.

It would therefore be advantageous to have an ankle orthosis which could be readily accommodated to the posterior portion of a user's lower leg and which would effectively transfer torque-producing forces from the foot to the tibia to prevent eversion an inversion but still retain substantially free dorsiflexion and plantar flexion. Such a device should be usable in medical and therapeutic applications, as postoperative uses. It should also be useful as a prophylactic device, such that it could be used by athletes in active sports to reduce or eliminate the need for prior practices such as taping. It would also be advantageous if the device were capable of being conveniently and comfortably used by anyone who wishes to prevent ankle injuries incurred during ordinary daily activities such as walking, climbing stairs, etc. Further, the device should be capable of being manufactured in a limited number of widely applicable sizes so that it can be readily used by anyone without having to go through tedious and expensive custom fitting of the device to each user.

BRIEF SUMMARY OF THE INVENTION

In accordance with the present invention there is provided an ankle orthosis having first force-transferring means for receiving a torque-producing force directed toward the region immediately adjacent the calcaneus and transmitting that force past the calcaneus toward the tibia. The first force-transferring means has at least two sections disposed respectively on the lateral and medial sides of the calcaneus, a single vertical riser means is disposed posteriorly of the calcaneus and is connected to both portions of the first force-transferring means to receive the force from the first force-transferring means and transfer the received force on to a second force-transferring means, a second force-transferring means is slidably attached to the proximal end of the riser means and is adapted to be attached to the distal portion of the user's leg to transfer the force from the riser to the tibia. The riser means is flexible in a sagittal plane but substantially rigid in a coronal plane such that upon application of torque-producing force to the calcaneus region the force is transferred to the tibia and dorsiflexion and plantar flexion of the ankle are permitted, but ankle inversion and eversion resulting from the application of the force are prevented.

In a preferred embodiment the first force-transferring means and the riser means are part of a unitary structure which also includes a cup-shaped member into which the user's heel is inserted.

In other preferred embodiments the orthosis device can be in the form of a shoe insert, attached to the heel of a shoe, or built into the body of a shoe. It may be used for medical or therapeutic purposes, as an aid in surgical recovery, or may be used by athletes and walkers to prevent injury during sports and other activities. It may also be used by persons with chronically weak ankles, as for instance elderly people, as an aid in their normal daily walking routines.

It can be manufactured in a few sizes, each of which will be useful and comfortable for a large number of users. The devices can thus be sold conveniently and economically through outlets such as medical supply stores and athletic equipment stores, since no difficult and expensive custom fitting is needed.

BRIEF DESCRIPTION OF THE DRAWINGS

FIG. 1 is a perspective view of one preferred embodiment of the device.

FIG. 2 is a cross sectional view taken on line 2—2 of FIG. 1.

FIG. 3 is a perspective view of another embodiment of the device.

FIG. 4 is a side elevation view of the device of FIG. 1 in use.

FIG. 5 is a side elevation view of an embodiment of the device attached to a shoe.

FIG. 6 is a side elevation view, partially cut away, of an embodiment of the device of this invention incorporated in a shoe structure.

FIGS. 7 and 8 are anterior and lateral (or medial) diagrams respectively of the human foot to illustrate the various ankle motions.

FIG. 9 is a schematic diagram based on a front elevation view of the device of FIG. 1 illustrating the torque and force transfer.

FIG. 10 encompasses three schematic diagrams (viewed toward the posterior side of the leg) illustrating the force effects on the structures of prior art AFO's and the device of this invention.

DETAILED DESCRIPTION-AND PREFERRED EMBODIMENTS

The ankle orthosis devices of this invention are best understood by reference to the drawings. The devices of this invention can be grouped into three embodiments; the self-contained or "shoe insert" embodiment of FIGS. 1 and 3, the "shoe attachment" embodiment of FIG. 5 and the "shoe incorporation" embodiment of FIG. 6. All function alike; the principal difference lies in the way in which the force-receiving and transferring element which surrounds the calcaneus is configured. The components of the device will be described with respect to the shoe insert embodiment of FIG. 1; analogous elements will be found in the other embodiments and those embodiments will be described only with respect to the differences in that component.

The basic element in the orthosis device is rib 10. Rib 10 is composed of a single vertical riser section 12 and two diverging lower sections 14, which meet at 16 to form an inverted Y shape. In the most preferred embodiment (as shown in FIG. 1) the rib 10 is molded or formed integrally with heel shell or cup 18, so that the entire rib/cup unit 11 is a unitary piece. In order to function properly the lower sections 14 of the rib 10 will be molded or formed as thicker portions in the walls of the cup 18, as illustrated at 15. The entire rib 10 is formed from a single piece of material so that there is no joint line at 16 where the riser section 12 meets the lower sections 14.

The cup portion 18 closely approximates the shape of the heel of a user's foot, and includes sides 22, bottom 24 and back 26. Back 26 preferably has some built-in conformity such as expansion groove 28 so as to facilitate a comfortable fit for a large variety of foot shapes and sizes.

FIG. 3 shows another embodiment in which the rib 10 and cup 18 are molded or formed separately and joined by rivets 32, adhesives or similar fastening means. Also shown in FIG. 3 is formation of the rib 10 by securely fastening the sections 12 and 14 at 16 by adhesives, rivets 33 or the like. Commonly this results in added thickness to the rib 10 at 16.

The rib 10 and cup 18 (whether formed separately or as an integral unit 11), as well as the leg connection member 36, may be made of any suitable material that provides the proper amount of flexibility. Flexibility for the rib 10, especially in the riser portion 12, means that the rib flexes in a sagittal plane but is substantially rigid for lateral/medial motion in a coronal plane. The degree of flexibility for any part will be dependent on the thickness of the material at that part, the type of material chosen and the leverage imparted by various lengths of the riser 12. The preferred material will be a plastic such as a polycarbonate, a polyethylene or a polypropylene polymer. Such materials are readily available in formulations that have varying degrees of rigidity following molding so that selection of a suitable material is easy for the manufacturer.

Alternatively the parts may be made of a flexible metal such as aluminum or stainless steel.

The back 26 of the cup 18 rises to a point approximately aligned with the distal end of the tibia. This height of the back is not critical and can be varied for the user's comfort. The central merged portion 16 of the rib 10 is normally aligned approximately with the top edge 30 of the cup 18. Preferably the merged portion 16 is slightly below the top 30 but the exact relationship is not critical.

If the rib 10 is formed separately from the cup 18, the lower sections 14 of the rib 10 are securely joined to the inner side of cup 18 by any convenient fastening means that will not cause discomfort to the user, such as adhesives or, as shown in FIG. 3, rivets 32. The inner sides of the rivets 32 are smooth so that the user's foot is not irritated. The same will be true of connections used to form a laminated rib 10 from separate riser 12 and sections 14.

In the shoe insert version of the present invention there are pads 34 secured to the outer sides 22 of 18. These pads are of a material which will provide a degree of adhesion to the inside of the shoe into which the orthosis is inserted. These may be of a tacky material, but preferably are adherent fiber mats of the type known as "hook and loop" fasteners. These prevent the orthosis from moving within the shoe and also serve as force transfer means which permit direct and positive transfer of forces from shoe to the rib/cup unit 11 and then on through the device to the tibia. This in effect makes the shoe part of the functioning of the device and assists in control of calcaneus motion and provides load management to the forefoot.

Slidably mounted at the top of riser 12 is a second force-transferring component, designated leg connection member or cuff assembly 36. This comprises a U-shaped shell 38 with a back portion 40 having a vertical hole 42 therethrough. Extending posteriorly from the back portion 40 and aligned centrally of the opening 42 is hollow rib 44. The upper or proximal end 46 of riser 12 extends into the opening 42 so that the riser normally makes contact with at least one surface of the inside of hole 42, but has enough clearance that the assembly 36 can slide freely vertically along the proximal end 46 of riser 12 (see FIG. 2) as indicated by arrows 50. Mounted at the top end 46 of riser 12 and extending posteriorly thereof is lug 48 which is adapted to move within the hollow channel 52 of rib 44. Within this channel 52 is located tension spring 54 which is secured at its upper end to lug 48 and at its lower end to the inside of rib 44, which may for this purpose be extended inwardly at its lower end as indicated at 56. Tension spring 54 serves to maintain a predetermined location for leg-securing assembly 36 with relation to riser 12. However, when the riser 12 is flexed by the motion of the user's foot tension spring 54 is extended and serves upon contraction to return the riser 12 and assembly 36 to their previous positions.

On the anterior side of assembly 36 shell 38 is formed into leg encasing wings 58. (It will be understood that while the wings 58 and shell 38 are shown as a unitary piece they may be separately molded and joined by any convenient means, such as adhesive, rivets, or like fasteners. Preferably they are molded with integral connectors for a simple snap or press fit.) The wings 58 extend anteriorly to approximately the lateral center line of the user's lower leg. For comfort it is preferred to include a generally U-shaped foam or cloth pad 60 on the inside of wings 58 and continuing therebetween, also to be secured by any convenient fastening means, such as adhesives or, as shown in FIG. 3, rivets 62.

The assembly 36 must be secured to the user's lower leg 63 for the device to be effective. This is accomplished by use of strap 64 shown in FIG. 4. One end of strap 64 is releasably adhered to the outer side of one of the wings 58. This is conveniently accomplished by having a "hook and loop" fastener 66 attached to the outer side of one wing 58. The inner side of one end of the strap 64 has a corresponding fastener so that the two can be securely attached. The leg strap 64 is then wound snugly around the user's lower leg 63 as indicated in FIG. 4 and the other end of the strap is secured to the strap's outer surface, preferably with two more mating "hook and loop" fastener surfaces. It is possible that the strap 64 could be permanently attached to the wing 58 as by rivets, but that would make it difficult to remove it for cleaning or to replace torn or frayed straps. Other types of releasable mechanical attachments, such as snaps, buttons or lugs could also be used but for convenience the "hook and loop" fasteners are most preferred. Similarly the end of the strap 64 could be secured by some form of buckle, but that does not permit the strap to be wound to a wide variety of different tightnesses. Also the presence of an external buckle can irritate the skin on the user's leg or can serve as a point of injury of someone else who comes into contact with the buckle as during a sporting event.

The strap 64 may be of any convenient material, which preferably is elasticized. While it would be possible to have an inelastic material for the strap 64, it has been found preferable for comfort and fit to use an elasticized material.

The vertical height of the leg encasing assembly 36 above the bottom 24 of the cup 18 is determined by a number of factors. These include the degree of flexibility of the rib, the amount it is intended to flex anteriorly and posteriorly, the leverage to be obtained from the device, the comfort of the user, the height of the user and the efficiency of the transfer of the force to the tibia through the muscle mass. A rib which extends higher has more leverage, but requires more material in the rib, in length and usually in thickness. In addition, it is more cumbersome and there may be some reluctance for a person to use it. On the other hand, if the rib is too short, it will have too little leverage to be as effective. We have found that an overall height of the orthosis from the bottom of the cup 18 to the top of the riser 12 in the range of 8–12 inches (20–30 cm) is quite satisfactory for users of a wide range of heights. Of course the device may be made taller or shorter as the user height and other conditions require.

An alternate form of the device of this invention is illustrated in FIG. 5. In this embodiment the lower sections 14 of the rib 10, rather than being secured to a cup 18, are secured to the outer side of a shoe 68. The distal end 70 of each section 14 is secured pivotally to the heel 72 of shoe 68 by pin 74. The user can then wear the shoe and walk with a normal gait for dorsiflexion and plantar flexion but is safe from the torque effects of lateral or medial impacts or stresses.

Yet another version of the present invention is shown in FIG. 6. In this embodiment the cup 18 attached to lower sections 14 is formed in the wall of a shoe 76, being encased by the back wall 80 of the shoe and the inner fabric layer 78 of the shoe 76.

The unique force transferring abilities of the orthosis device of this invention are illustrated in FIGS. 9 and 10. Center line 82 represents a sagittal plane center line of the device and the user's leg, ankle and foot. A force applied vertically along the center line, as for instance the upward force when a normal walking or running step is taken, causes no lateral or medial torque and therefore has no tendency to cause undue inversion or eversion. The important dorsiflexion and plantar flexion movements are not restricted, since those movements act along the center line and are necessary to provide the propulsive and recovery motions of walking and running. In the device of the present invention the user's foot can move freely in the sagittal plane encompassing center line 82. A small degree of normal inversion and eversion is also possible since the foot itself is not secured to the cup 18 or shoes 68 or 76.

When a substantial force is applied off the center line 82 to the distal (plantar), medial or lateral side of the calcaneus, however, a torque is imposed on the ankle which causes excessive eversion or inversion. In the device of the present invention that torque-creating force is received by the cup 18 or shoes 68 or 78 and sections 14. The torque-producing force is then transmitted upwardly through sections 14 to riser 12 as indicated by arrows 84. Riser 12 in turn transfers the force to leg connection assembly 36 and then through strap 64 to the lower leg and tibia, which is much more capable of withstanding the force than is the ankle. The ankle then is essentially entirely bypassed and receives no significant portion of the torque-producing force, and thus has little tendency to rotate in inversion or eversion.

As illustrated in FIG. 10A, the device of the present invention has a triangular configuration and therefore is a highly effective means of transferring forces applied off the centerline of the ankle to the tibia, as indicated by the force transfer arrows. The triangular shape provides no pivot points which would distort the unit and reduce its force-transferring ability. The present device is capable of transmitting the full torque-producing force regardless of where the torque producing blow occurs off the center line 82, since that force is received by the cup 18 or rigid heel 72 of shoe 68 or 78 and transferred directly to the integral or rigidly connected sections 14, from which it is transferred on through the device to the tibia.

By comparison, the prior art leg brace AFO's, which as noted above have a parallelogram configuration shown in FIG. 10B, have pivot points at 70 and can distort from the torque, as shown in phantom. Similarly, those prior art AFO's which include only a single posterior brace, and thus have a "vertical rod" configuration as shown in FIG. 10C, tend to rotate coaxially with the foot, increasing inversion or eversion, and are unable to transfer such torque producing forces unless they are attached to an extremely rigid shoe. Even then the point of attachment is a source of weakness for there is very little bending moment resistance at such center line attachment and the forces, rather than being smoothly transmitted as through the section 16 of the rib 10 in the present invention, are applied fully against attaching means such as clamps. Substantial forces often cause such attaching means to part so that the AFO is rendered essentially useless. In addition, the use of such extremely rigid shoes provides much discomfort for the wearer and severely restricts the ability to walk with a normal gait.

It will be evident that there are many embodiments of this invention which are not specifically described above, but which are clearly within the scope and spirit of the invention. The above description is therefore intended to be exemplary only, and the scope of the invention is to be defined solely by the appended claims.

We claim:

1. An ankle orthosis comprising:
    first force-transferring means for receiving a torque-producing force directed toward the region immediately adjacent the calcaneus of the foot of a user and transmitting that force past said calcaneus toward the tibia, said first force-transferring means having at least two sections disposed respectively on the lateral and medial sides of said calcaneus each of said sections being directed generally posteriorly from a first point adjacent to the lateral or medial side of the calcaneus to a second point, posterior to and above the calcaneus, the two sections joining at the second point;
    vertical riser means disposed posteriorly of and above said calcaneus and connected to both sections of said first force-transferring means at the second point to receive said force from said first force-transferring means and transfer said received force on to a second force-transferring means, the vertical riser means and the first force transferring means forming an inverted y; and
    second force-transferring means attached to the proximal end of said riser means and adapted to be attached to the distal portion of said user's leg to transfer said force from said riser to the tibia;
    said riser means being flexible in a sagittal plane but substantially rigid in a coronal plane such that upon application of torque-producing force to said calcaneus region said force is transferred to said tibia and dorsiflexion and plantar flexion of said ankle are freely permitted but ankle inversion and eversion resulting from said application of said force are substantially prevented.

2. An ankle orthosis as in claim 1 wherein said first force-transferring means and said riser means are part of a unitary structure.

3. An ankle orthosis as in claim 1 wherein said first force-transferring means further comprises cup means for receiving and partially surrounding said calcaneus, wherein the two sections are attached respectively to lateral and medial sides of said cup means.

4. An ankle orthosis as in claim 3 wherein said cup means, said two sections and said riser are formed integrally as part of a unitary structure.

5. An ankle orthosis as in claim 3 wherein said two sections and said riser are formed as part of a unitary rib structure, said cup means is formed separately and said rib structure and said cup are fastened together to form a connected structure.

6. An ankle orthosis as in claim 3 wherein said cup means, said two sections and said riser are formed separately and are fastened together to form a connected structure.

7. An ankle orthosis as in claim 1 wherein said second force-transferring means comprises a housing with a vertical opening therethrough in which said proximal end of said riser means is disposed, and guide means within said housing which cooperates with means on said riser means to maintain a vertical sliding relationship between said riser means and said second force-transferring means.

8. An ankle orthosis as in claim 3 wherein said cup means comprises a heel-receiving member having a shape which corresponds generally to the lateral sides, posterior and plantar portion of a user's foot adjacent said calcaneus and is otherwise open to permit the user to insert said foot and seat it in said cup means, said cup means being adapted to be placed inside the heel portion of a shoe.

9. An ankle orthosis as in claim 8 further comprising attaching means on the lateral surfaces of said cup means to permit said orthosis to be releasably secured to the inside of said shoe to permit use of said orthosis by a user while wearing said shoe.

10. An ankle orthosis as in claim 3 wherein said cup means comprises a heel-receiving member having a shape which corresponds generally to the lateral sides, posterior and plantar portion of a user's foot adjacent said calcaneus and is otherwise open to permit the user to insert said foot and seat it in said cup means, said member being an integral part of the structure of a shoe.

11. An ankle orthosis as in claim 3 wherein said two sections of said first force-transferring means are secured at their distal ends respectively to the lateral and medial sides of a shoe having a substantially rigid heel and a substantially rigid heel portion of its upper body, said cup means comprising said heel portion of said upper body.

12. An ankle orthosis as in claim 7 wherein said housing further comprises a U-shaped member defining a vertical opening therethrough as a channel of the "U", said U-shaped member opening anteriorly and adapted to encircle the posterior portion of the user's lower leg, and a strap means attached to the outer surface of said U-shaped member.

13. An ankle orthosis as in claim 3 wherein the distance from the bottom of said cup means to the top of said riser means is on the order of 8–12 inches.

14. An ankle orthosis as in claim 3 wherein said cup means has integrated therein, in location exterior to the cup, pads to facilitate secure fit of said orthosis into a variety of shoe shapes that respectively fit a variety of different sizes and shapes of users' feet.

15. An ankle orthosis as in claim 1 wherein the second force-transferring means is slidably attached to the proximal end of said riser means.

16. An ankle orthosis as in claim 7 wherein said housing further comprises:
   resilient means within said housing and connected to said housing and said riser means to cause said riser means and said housing to return to a predetermined position relative to each other after having been moved from said position by sliding relative to each other.

17. An ankle orthosis as in claim 7 wherein said housing further comprises:
   strap means connected to said housing and adapted to be wrapped snugly around the distal portion of a user's lower leg and to transfer forces reaching said housing to the user's tibia.

18. An ankle orthosis as in claim 16 wherein said resilient means comprises a tension spring disposed in said guide means and connected at its ends respectively to the proximal end of said riser means and the interior of said guide means.

19. An ankle orthosis as in claim 18 wherein said guide means comprises a vertical groove on the inner posterior surface of said vertical opening in said housing, said riser means has lug means extending posteriorly outwardly from the surface thereof and projecting into said groove, and said spring is attached at its ends respectively to said lug means and the distal end of said groove.

20. An ankle orthosis as in claim 17 wherein said strap means comprises a band having on the surface thereof means to releasably attach at one end to said housing and at the other end to its own surface.

21. An ankle orthosis as in claim 20 wherein said strap means has some degree of elasticity.

22. An ankle orthosis comprising:
   first force-transferring means for receiving torque-producing forces directed toward the region immediately adjacent the calcaneus of the foot of a user resulting from movement of a human foot and ankle and for transmitting these forces past said calcaneus toward the tibia, said first force-transferring means having at least two sections disposed respectively on the lateral and medial sides of said calcaneus each of said sections being directed generally upwardly and posteriorly from a first point adjacent to the lateral and medial side of the calcaneus to a second point posterior to and above the calcaneus, the two sections joining at the second point;
   vertical riser means disposed posteriorly of said calcaneus and connected to each of said sections of said first force-transferring means at the second point for receiving said forces from said first force-transferring means and for transferring said received forces on to a second force-transferring means; and
   second force-transferring means slidably attached to the proximal end of said riser means for selectively receiving from said riser substantially only such components of said forces as are substantially transverse to the vertical riser, and for attaching to the distal portion of said user's leg to transfer so much of said forces as are selectively received form said riser to the tibia;
   wherein said slidable attachment of said second force-transferring means to said riser means prevents forces resulting from dorsiflexion and plantar flexion of said ankle from transferring from said riser means to said second force-transferring means and dorsiflexion and plantar flexion of said ankle are substantially freely permitted; and
   wherein said slidable attachment of said second force-transmitting means to said riser means permits forces resulting from inversion and eversion of said ankle to transfer from said riser means to said second force-transferring means and inversion and eversion of said ankle are substantially prevented.

23. An ankle orthosis for substantially preventing eversion and inversion of the ankle while permitting substantially free plantar flexion of the ankle in a sagittal plane, the orthosis comprising:
   a calcaneus-embracing element having two sections, one section being disposed on a lateral side and another section being disposed on a medial side of a user's calcaneus, the two sections joining at one point, the point being located substantially posterior to and above the calcaneus, and the two sections transmitting at least the forces directed toward the calcaneus and resulting in eversion and inversion of the user's ankle away from the calcaneus to the point posterior of the calcaneus where the two rigid members join;

a leg-embracing element, adapted to be attached about the user's leg and to extend to a distal position therefrom, for substantially coupling forces experienced at the distal position into the user's leg; and a vertical riser element, connecting to the calcaneus-embracing element at the point posterior to and above the calcaneus where the two sections join and to the leg-embracing element at its portion extending distally to the user's leg, for substantially coupling the forces resulting in both eversion and inversion of the user's ankle from the calcaneus-embracing element to the leg-embracing element, whereby eversion and inversion of the user's ankle are substantially prevented while plantar flexion of the user's ankle is permitted to transpire substantially freely.

24. The ankle orthosis according to claim 23 wherein the calcaneus-embracing element comprises:

a cup having sections embracing a lateral side and a medial side and a base of user's calcaneus.

* * * * *